(12) United States Patent
Justice et al.

(10) Patent No.: US 9,701,934 B2
(45) Date of Patent: Jul. 11, 2017

(54) CULTURE VESSEL AND METHOD OF GROWING CELLS IN CULTURE VESSEL

(75) Inventors: Brad Justice, Reno, NV (US); Paul Iazzetti, Allston, MA (US)

(73) Assignee: GLOBAL CELL SOLUTIONS, LLC, Charlottesville, VA (US)

(*) Notice: Subject to any disclaimer, the term of this patent is extended or adjusted under 35 U.S.C. 154(b) by 117 days.

(21) Appl. No.: 13/574,636

(22) PCT Filed: Jan. 21, 2011

(86) PCT No.: PCT/US2011/022025
§ 371 (c)(1),
(2), (4) Date: Nov. 21, 2012

(87) PCT Pub. No.: WO2011/091233
PCT Pub. Date: Jul. 28, 2011

(65) Prior Publication Data
US 2013/0059376 A1    Mar. 7, 2013

Related U.S. Application Data

(60) Provisional application No. 61/297,514, filed on Jan. 22, 2010.

(51) Int. Cl.
| | |
|---|---|
| *C12M 1/02* | (2006.01) |
| *C12M 1/42* | (2006.01) |
| *C12N 1/20* | (2006.01) |
| *C12N 5/071* | (2010.01) |
| *C12M 1/12* | (2006.01) |

(52) U.S. Cl.
CPC ............ *C12M 27/00* (2013.01); *C12M 25/16* (2013.01)

(58) Field of Classification Search
USPC .................. 137/574, 576; 220/563; 366/339; 435/252.1, 289.1, 366
IPC ........... B01F 5/06; B06K 15/077; C12M 1/02, 1/42; C12N 1/20, 5/071
See application file for complete search history.

(56) References Cited

U.S. PATENT DOCUMENTS

| | | | |
|---|---|---|---|
| 5,407,809 A  * | 4/1995 | Finn ................................ 435/41 |
| 2005/0054101 A1* | 3/2005 | Felder et al. ................. 435/383 |
| 2008/0277009 A1* | 11/2008 | Sprague ................ B01F 5/0451 138/38 |
| 2009/0148941 A1* | 6/2009 | Florez et al. ................. 435/325 |
| 2009/0161483 A1* | 6/2009 | Ramhorst ........... B01F 7/00133 366/339 |

FOREIGN PATENT DOCUMENTS

WO    WO 2005018899 A1 *  3/2005

\* cited by examiner

*Primary Examiner* — Debbie K Ware
*Assistant Examiner* — Kailash C Srivastava
(74) *Attorney, Agent, or Firm* — Vance Intellectual Property, PC

(57) ABSTRACT

A culture vessel and a method of growing cells in a culture vessel. The culture vessel includes a container and a plurality of agitators. The container receives a medium and cells. The plurality of agitators is positioned to contact the medium when received in the container and configured to promote suspension of the cells in the medium upon oscillation of the agitators. The agitators are at least one of coupled to and formed integrally with the container such that there is no relative movement therebetween. The method includes receiving a medium and cells in a container and oscillating the medium such that the cells traverse along a longitudinal direction of the container.

11 Claims, 19 Drawing Sheets

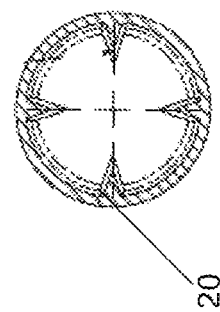
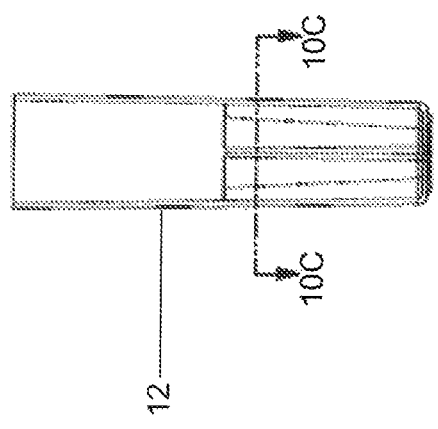
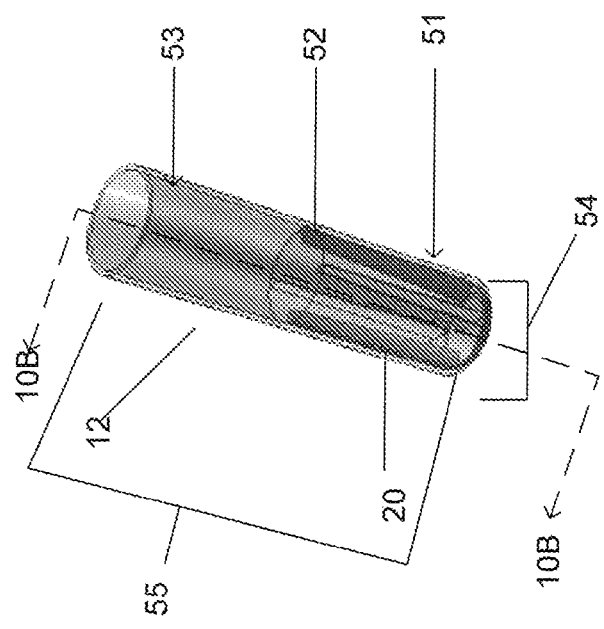

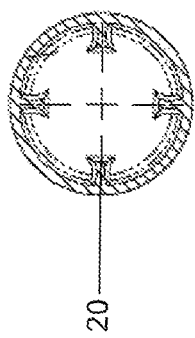
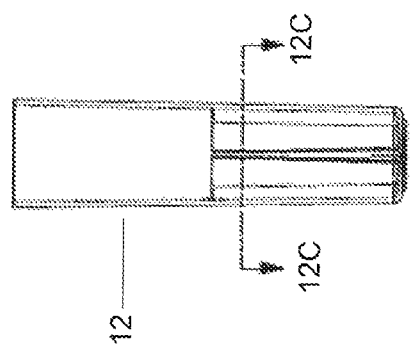
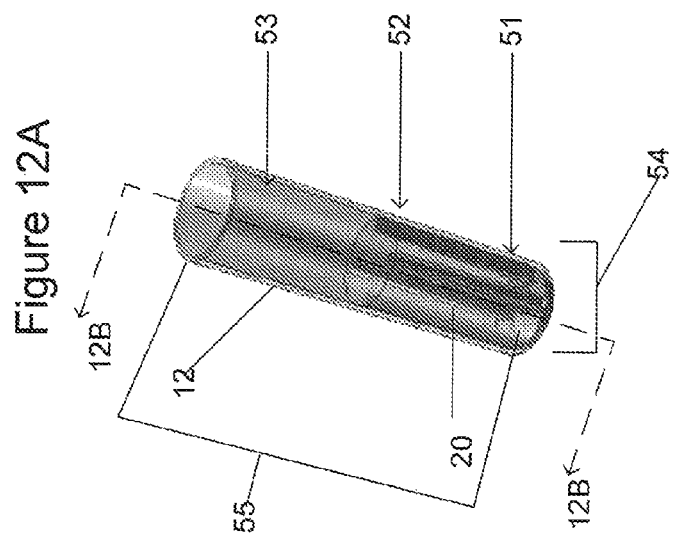

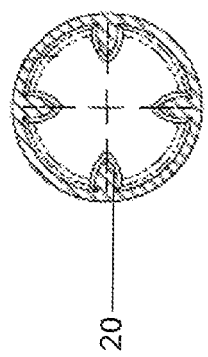
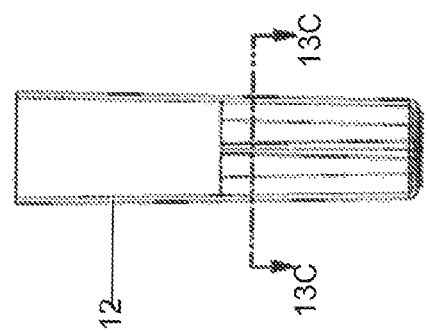
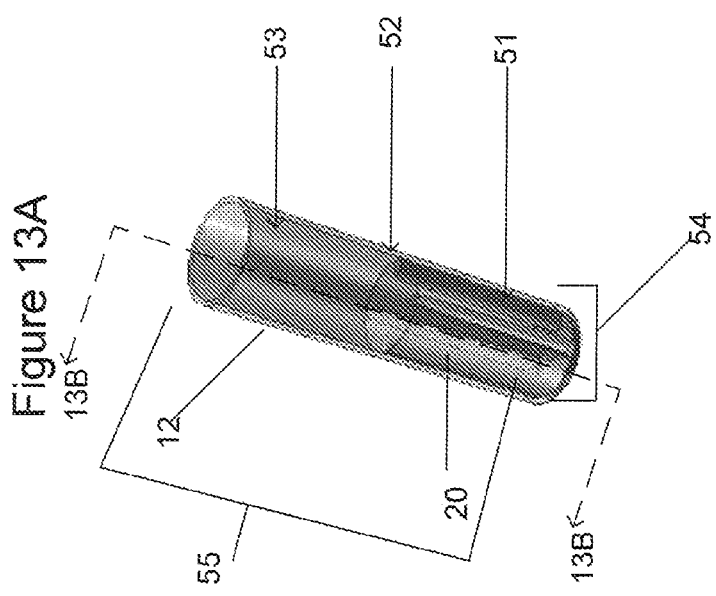

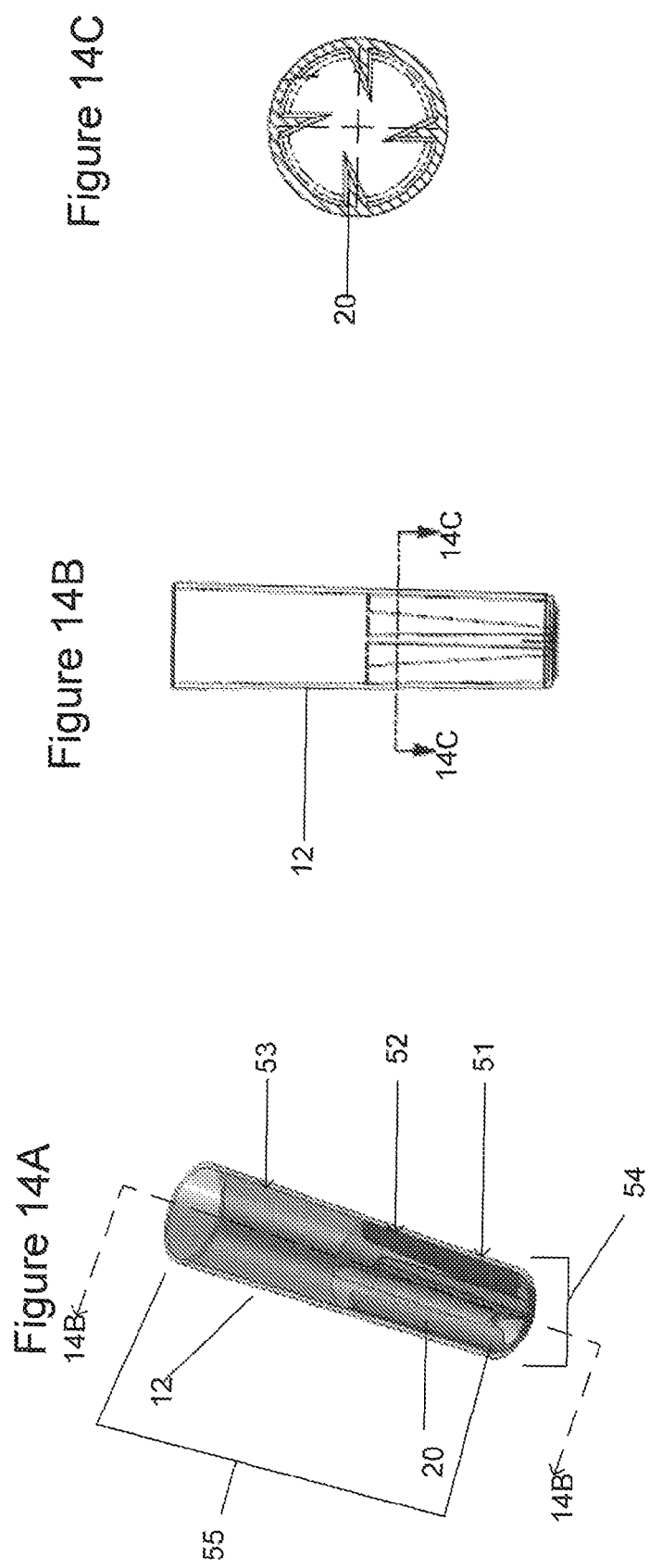

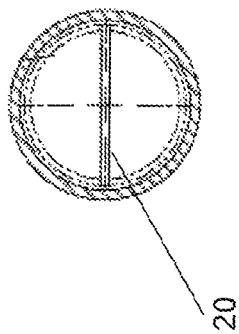
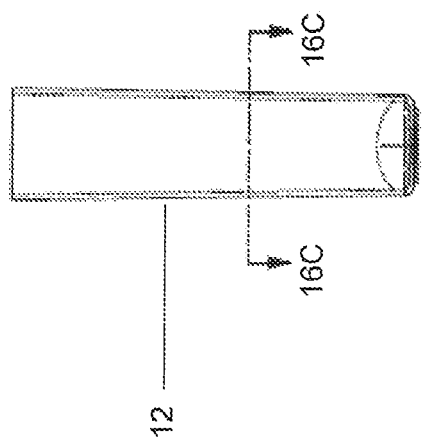
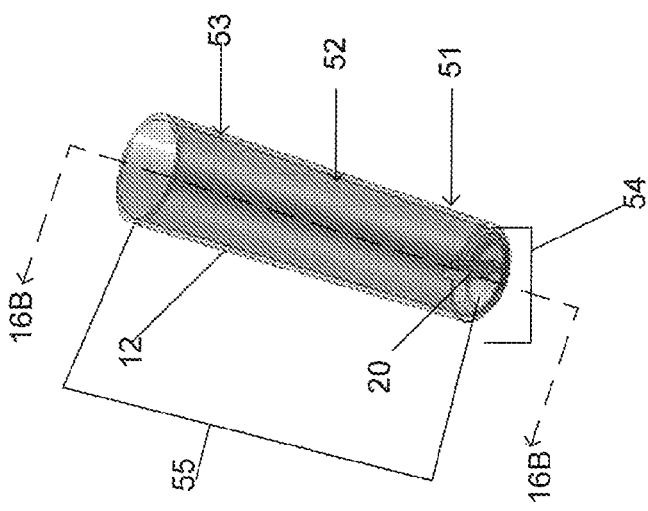

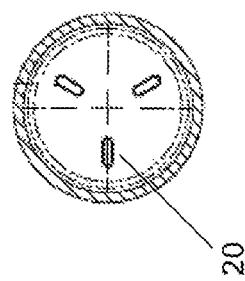
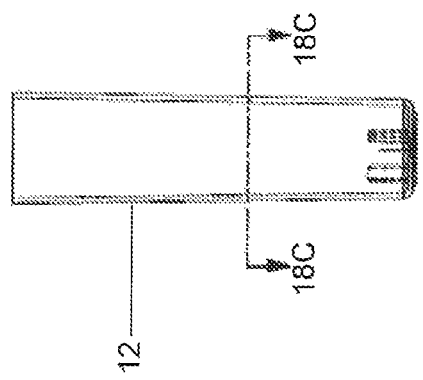
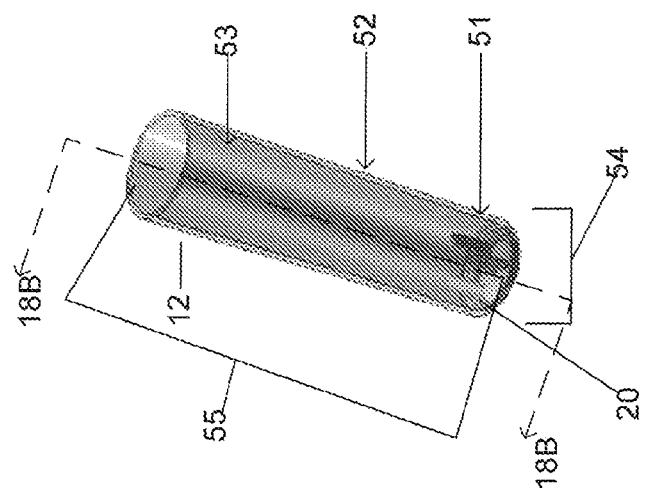

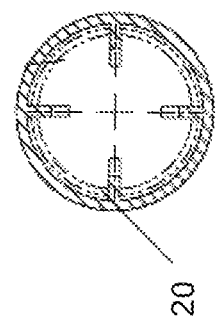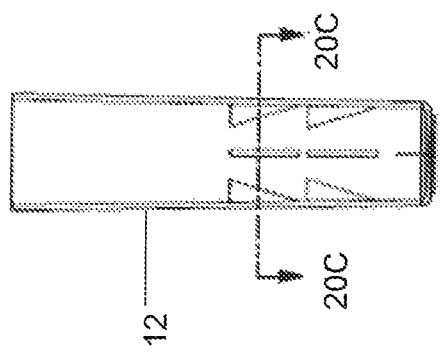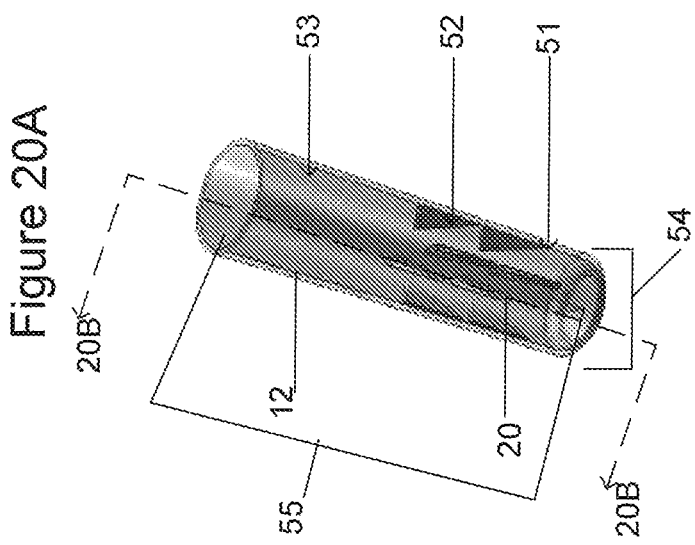

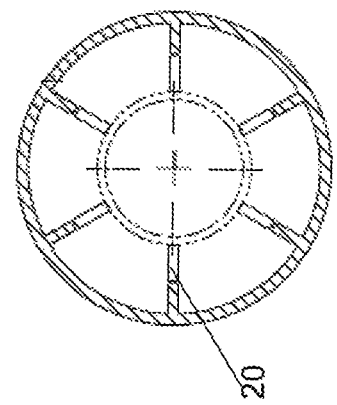
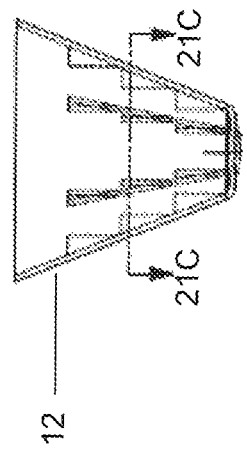
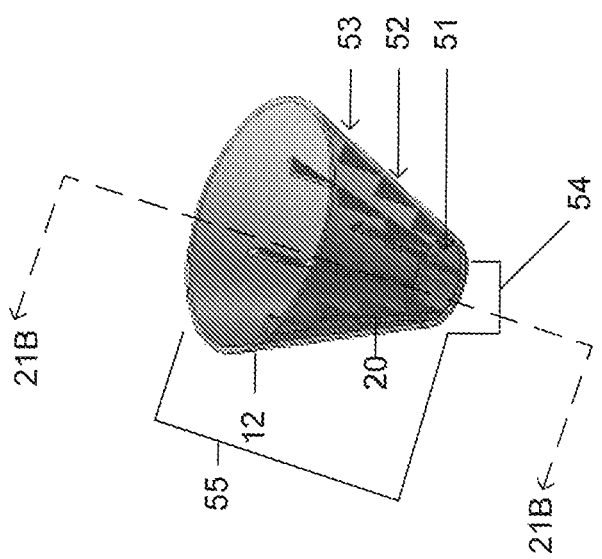

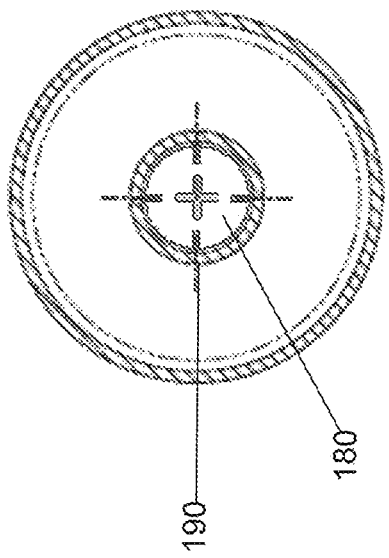
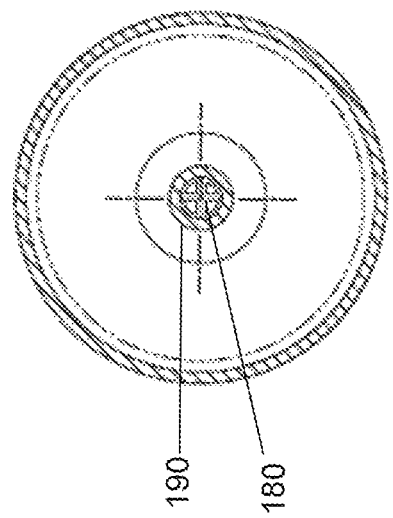
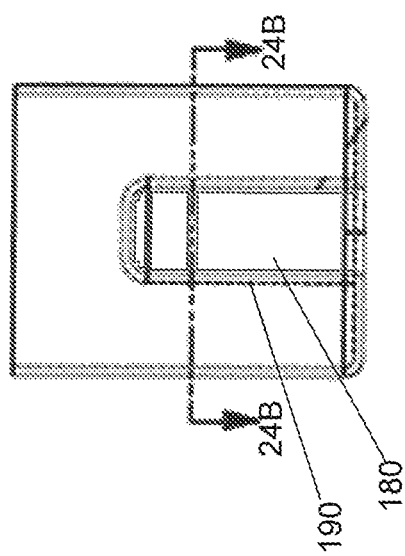
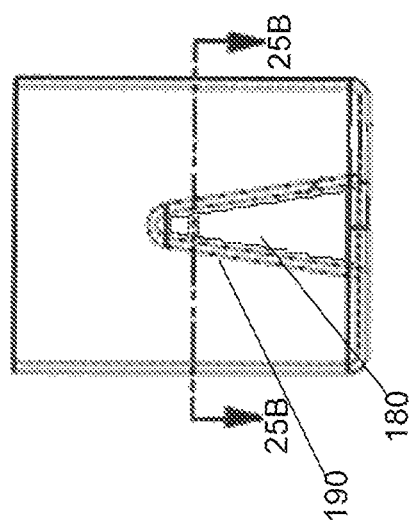

CULTURE VESSEL AND METHOD OF GROWING CELLS IN CULTURE VESSEL

BACKGROUND

Field of Embodiments

The disclosed embodiments relate generally to a culture vessel and a method of growing cells in a culture vessel.

Description of Related Art

Cell culture is a laboratory process used primarily for the growth, propagation, and production of cells for analysis or the production and harvesting of cell products.

Traditional culture vessels often use flat bottom dishes to grow cells of interest. Flat bottom dishes, such as flasks or Petri dishes or roller bottles, provide a limited surface on which cells can attach and grow.

Other culture vessels use microcarriers to grow cells of interest. Microcarriers increase the volume available on which cells can grow. Microcarriers may be suspended in a growth media in a culture vessel to give the cells on the microcarriers access to oxygen and other nutrients needed for the cell growth. Microcarriers may be stirred or agitated to keep them suspended in the growth media and promote cell growth on their surface. Alternatively, microcarriers and culture medium may contact a chamber placed on a rocking platform where the rocking motion of the platform induces waves in the culture medium, thereby causing oxygen transfer to promote cell growth on the surface of the microcarriers (e.g., a GE Wave system). Or, for example, a packed bed or flow-through reactor system may pump the culture medium so that nutrients required to promote cell growth may be provided to microcarriers located within the packed bed or flow-through reactor system.

Conventional mechanisms used to stir microcarriers and maintain them in suspension include a spinner flask, a tissue culture container, and the incorporation of various geometries in the walls of a rotating element within a bioreactor. A spinner flask may include a culture vessel and a suspended impeller positioned inside the culture vessel. The suspended impeller may be driven by an external rotating magnet positioned under the base of the culture vessel to cause the suspended impeller to rotate within the culture vessel and maintain the microcarriers in suspension. A tissue culture container, for example TPP's tissue culture and centrifuge tube, may allow for culture growth when the tubes are placed in racks and then into an incubator; the tubes may be shaken while in the incubator. The incorporation of veins of various geometries in the walls of a rotating element within a bioreactor is designed for large scale production environments. The incorporation of veins of various geometries in the walls of a rotating element within a bioreactor also requires a fixed stirred element, disassembly for cleaning, and a flow through system. Conventional mechanisms, such as the two previously mentioned, may impart hydrodynamic stress, such as excessive shear or acceleration forces or eddies, on growing cells, that can damage or alter the structure of the growing cells. For more information on shear forces please see the article entitled "Physical Mechanisms of Cell Damage in Microcarrier Cell Culture Bioreactors," published on Nov. 30, 1987 and herein incorporated by reference.

Conventional mechanisms also may include a magnetic impeller. The magnetic impeller may include a paddle and an integrated magnet. The integrated magnet provides a smooth, even rotation at required speeds on a magnetic stirrer. Magnet microcarriers placed in such conventional mechanisms may get stuck, for example, to the magnetic paddle or be drawn, for example, toward the bottom of the spinner flask where the magnetic stirrer is positioned. This attraction prevents the cells on the magnetic microcarriers from obtaining proper nutrients to grow. Conventional mechanisms, like the magnetic impeller, may also prevent cell separation beads from properly separating single cells suspended in the spinner flask. Separation beads, such as Dynal beads from LIFE technologies or MACS Microbeads from Miltenyi Biotec, are attracted to the magnetic paddle or are drawn toward the bottom of the spinner flask where the magnetic stirrer is positioned, for example, because of the magnetic properties of the separation beads. This attraction prevents the separation beads from properly separating any single cells suspended in the spinner flask.

There is a particular need for stirring and particle dispersing actions to be inherent in a disposable bioreactor tube or vessel, which is currently not addressed. The disposable bioreactor tube or vessel may have enhancements such as sterility for cell culture, specialized closures, and other benefits above and beyond the critical element of stirring. For example, in order for a liquid handling tool, such as a pipette, to access the bottom of the vessel, the stirring elements must be arranged to allow access to the bottom of the tube where the bioreacted material may accumulate. A need exists for an improved technology that addresses issues such as, for example, the disadvantages of the conventional mechanisms noted above.

SUMMARY

One embodiment relates to a culture vessel. The culture vessel comprises a container and a plurality of agitators. The container receives a medium and cells. The plurality of agitators is positioned to contact the medium when received in the container and configured to promote suspension of the cells in the medium upon oscillation of the agitators. The agitators are at least one of coupled to and formed integrally with the container such that there is no relative movement therebetween.

Another embodiment relates to a method of growing cells in a culture vessel. The method includes receiving a medium and cells in a container and oscillating the medium such that the cells traverse along a longitudinal direction of the container.

Another embodiment relates to a culture vessel. The culture vessel comprises a container and a sheet. The container receives a medium and cells. The sheet is inside of the container. The sheet includes a plurality of agitators. The plurality of agitators are positioned to contact the medium when received in the container and are configured to promote suspension of the cells in the medium upon oscillation of the agitators. The sheet is configured to couple to an inner surface of the container such that there is no relative movement therebetween.

Yet another embodiment relates to a sterilized package. The sterilized package comprises a sheet and a plurality of agitators. The sheet is for coupling to an inner surface of a culture vessel. The plurality of agitators are configured to contact a medium received in the culture vessel and are configured to promote suspension of cells in the medium. The agitators are included on the sheet.

In another embodiment, the invention is drawn to a sheet for coupling to an inner surface of a culture vessel; comprising a plurality of agitators, configured to contact a medium received in the culture vessel and configured to promote suspension of cells in the medium, included on the sheet.

BRIEF DESCRIPTION OF THE DRAWINGS

These and other features, aspects, and advantages of the disclosed embodiments will become apparent from the following description, appended claims, and the accompanying exemplary embodiments shown in the drawings, which are briefly described below.

FIG. 10A is a top, side, perspective view of an embodiment of a culture vessel including a plurality of agitators.

FIG. 10B is a side, cross sectional view of the culture vessel of FIG. 10A taken along 10B-10B.

FIG. 10C is a top, cross-sectional view of the culture vessel of FIG. 10B taken along line 10C-10C.

FIG. 12A is a top, side, perspective view of an embodiment of a culture vessel including a plurality of agitators.

FIG. 12B is a side, cross sectional view of the culture vessel of FIG. 12 taken along 12B-12B.

FIG. 12C is a top, cross sectional view of the culture vessel of FIG. 12B taken along line 12C-12C.

FIG. 13A is a top, side, perspective view of an embodiment of a culture vessel including a plurality of agitators.

FIG. 13B is a side, cross sectional view of the culture vessel of FIG. 13A taken along line 13B-13B.

FIG. 13C is a top, cross sectional view of the culture vessel of FIG. 13B taken along line 13C-13C.

FIG. 14A is a top, side, perspective view of an embodiment of a culture vessel including a plurality of agitators.

FIG. 14B is a side, cross sectional view of the culture vessel of FIG. 14A taken along line 14B-14B.

FIG. 14C is a top, cross sectional view of the culture vessel of FIG. 14B taken along line 14C-14C.

FIG. 16A is a top, side perspective view of an embodiment of a culture vessel including a plurality of agitators.

FIG. 16B is a side, cross sectional view of the culture vessel of FIG. 16A taken along line 16B-16B.

FIG. 16C is a top, cross sectional view of the culture vessel of FIG. 16B taken along line 16C-16C.

FIG. 18A is a top, side perspective view of an embodiment of a culture vessel including a plurality of agitators.

FIG. 18B is a side, cross sectional view of the culture vessel of FIG. 18A taken along line 18B-18B.

FIG. 18C is a top, cross sectional view of the culture vessel of FIG. 18B taken along line 18C-18C.

FIG. 20A is a top, side perspective view of an embodiment of a culture vessel including a plurality of agitators.

FIG. 20B is a side, cross sectional view of the culture vessel of FIG. 20A taken along line 20B-20B.

FIG. 20C is a top, cross sectional view of the culture vessel of FIG. 20B taken along line 20C-20C.

FIG. 21A is a top, side perspective view of an embodiment of a culture vessel including a plurality of agitators.

FIG. 21B is a side, cross sectional view of the culture vessel of FIG. 21A taken along line 21B-21B.

FIG. 21C is a top, cross sectional view of the culture vessel of FIG. 21B taken along line 21C-21C.

FIG. 24A is a side, cross sectional view of an embodiment of a culture vessel that includes a magnetic insert.

FIG. 24B is a top, cross sectional view of the culture vessel of FIG. 24A taken along line 24B-24B.

FIG. 25A is a side, cross sectional view of an embodiment of a culture vessel that includes a magnetic insert.

FIG. 25B is a top, cross sectional view of the culture vessel of FIG. 25A taken along line 25B-25B.

DETAILED DESCRIPTION OF THE PREFERRED EMBODIMENTS

Figure 1:
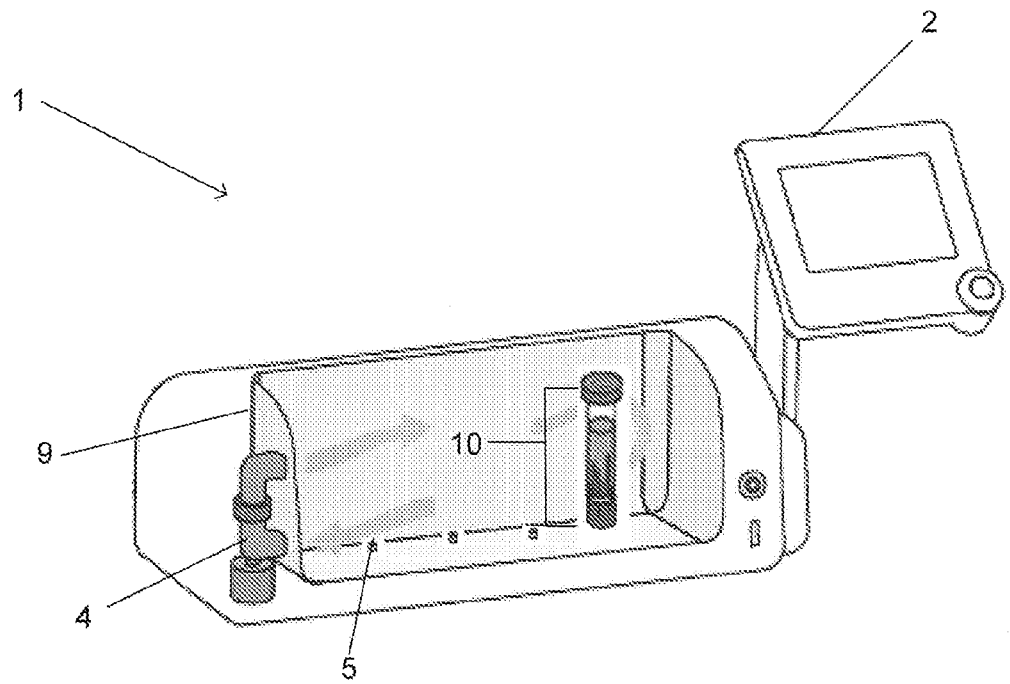
FIG. 1 is a top, front, perspective view of an exemplary biolevitator including an embodiment of a culture vessel.

Presently preferred embodiments are illustrated in the drawings. An effort has been made to use the same or like reference numbers throughout the drawings to refer to the same or like parts. Although the specification refers primarily to biolevitator systems, it should be understood that the subject matter described herein may be applicable to any cell system that stirs or agitates media to promote cell growth in a culture vessel.

Overview of a Biolevitator System

Figure 2:
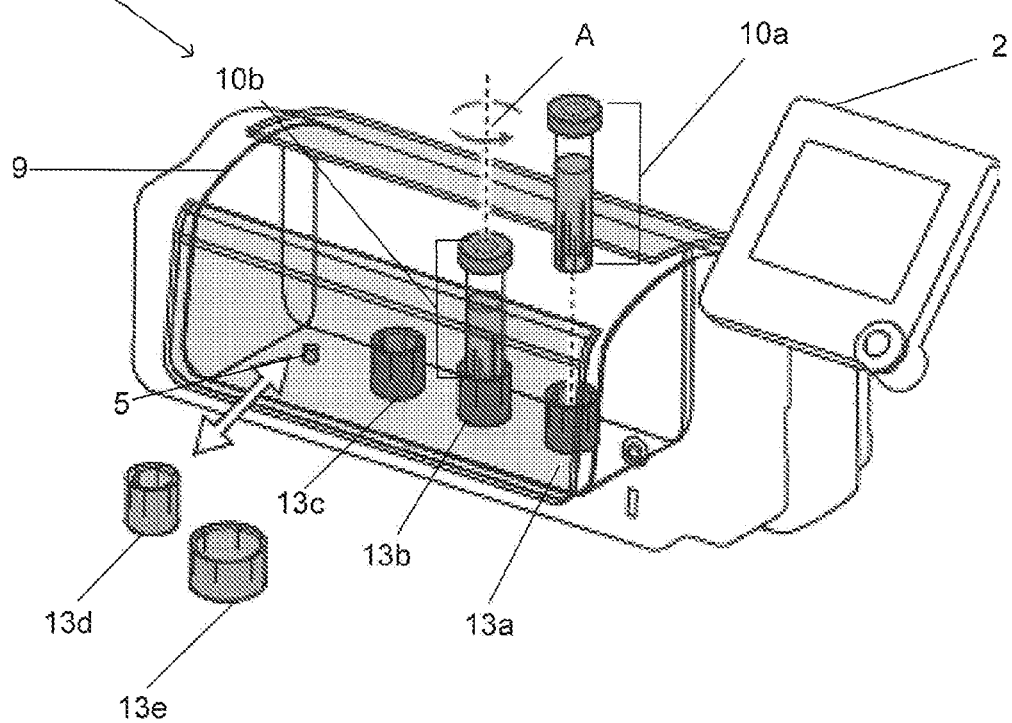
FIG. 2 is a top, front, perspective view of an exemplary biolevitator including a plurality of culture vessels according to an embodiment.
Figure 3:
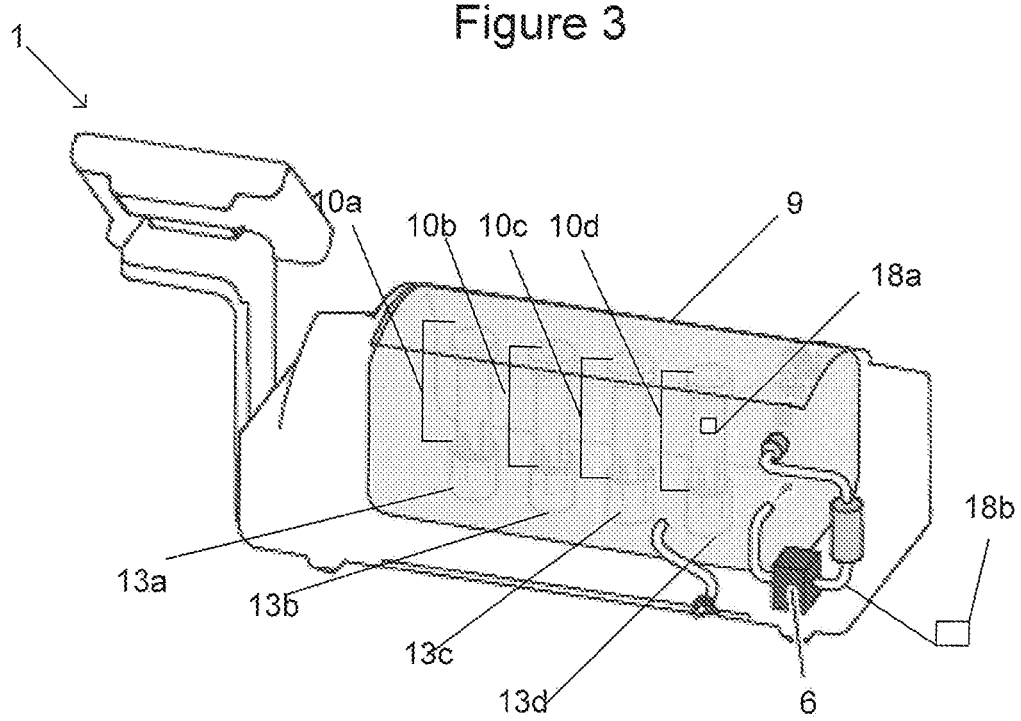
FIG. 3 is a top, rear, perspective view of an exemplary biolevitator.

A biolevitator 1 may be used to grow cells under conditions optimized for cell growth. Referring to FIGS. 1-3, a biolevitator 1 may include a chamber 9, a motion generating device 5, a monitoring system 6, a channel 4, and a control system 2. The elements previously mentioned as being included in a biolevitator are merely exemplary elements that may be included in a biolevitator, and are not limiting of what a biolevitator must or can include.

The chamber 9 of the biolevitator 1 houses the cells to be grown and any medium that promotes cell growth. The chamber 9 may include one or more culture vessels 10 and one or more holders 13. In this application, the reference numerals 10 and 13 are used generically to refer to a culture vessel and a holder respectively; the reference characters 10a, 10b, 10c, etc. are used to distinguish between specific culture vessels; and the reference characters 13a, 13b, 13c, etc. are used to distinguish between specific holders.

The culture vessels 10a, 10b receive and hold the medium with the cells to be grown in the chamber 9. When desired, the cells may be extracted from the culture vessels 10a, 10b. The medium included may be directly provided to each culture vessel 10a, 10b (e.g., pipetting of fluid into each culture vessel 10a, 10b) or may be directly provided to the chamber 9 and indirectly provided to each culture vessel 10a, 10b (e.g., providing oxygen into the chamber 9, which diffuses into each culture vessel 10a, 10b). Both can be done, for example, through conventional techniques.

The holders 13a, 13b, 13c, 13d, 13e can be designed to secure the culture vessels 10 within the chamber 9 and to protect electronics and mechanical components of the biolevitator 1 from accidental spills occurring within the chamber 9. The holders 13a, 13b, 13c, 13d, 13e may be any suitable size or shape, so as to be able to hold culture vessels 10a, 10b of various sizes and shapes. As shown, for example in FIG. 2, the holders 13a, 13b may secure the culture vessels 10a, 10b respectively or as shown, for example in FIG. 3, the holders 13a, 13b, 13c, 13d may secure the culture vessels 10a, 10b, 10c, 10d respectively. Not all holders, however, may secure a culture vessel. For example, as shown in FIG. 2, a holder 13c may be empty. The holders 13 may be a variety of sizes and shapes. For example, as shown in FIG. 2, holder 13d has a smaller diameter than holder 13e.

The motion generating device 5 of the biolevitator 1 can generate motion, i.e., stir or agitate the cells in the media), within each culture vessel 10 to promote growth of the cells inside each culture vessel 10. The motion generating device 5 may connect indirectly or directly to the culture vessel 10. For example, as shown in FIG. 2, a drive shaft of a motion generating device 5 may be coupled to a holder 13, such that when the motion generating device 5 generates motion, the coupling of the drive shaft of the motion generating device to the holder 13 causes the holder 13 to move and the culture vessel 10 secured within the holder 13 to move. The holder 13 may be coupled to the drive shaft of the motion generating device 5 by any suitable mechanism. (e.g., a holder 13 may be spring loaded onto the drive shaft of the motion generating device 5). In another example, the motion generating device 5 may be directly coupled to gears included in a channel of the culture vessel 10, such that the motion generating device 5 causes the culture vessel 10 to move (not shown). Also, for example, the motion generating device 5 may be a linear drive that pushes and pulls the culture vessel 10 along a path of gears integrated into the culture vessel 10 (not shown).

The motion generating device 5 causes each culture vessel 10a, 10b to rotate around an axis A positioned in the center of each culture vessel 10a, 10b. Although this application refers to one motion generating device 5, it is understood that there may be one or more motion generating devices 5. If there are a plurality of motion generating devices, each motion generating device 5 may connect to a separate culture vessel 10a, 10b. Although FIG. 2 shows the motion generating device 5 causing each culture vessel 10a, 10b to rotate unidirectionally, the motion generating device 5 may cause each culture vessel 10a, 10b to rotate bidirectionally. Additionally, although FIG. 2 shows the motion generating device 5 causing each culture vessel 10a, 10b to rotate in a counterclockwise direction, the motion generating device 5 may cause each culture vessel 10a, 10b to rotate in a clockwise direction when each culture vessel 10a, 10b rotates unidirectionally.

The monitoring system 6 can be configured to view, measure, record, and transmit data to the control system 6 to ensure that the cells are properly growing and that the desired amount of nutrients needed for the cells to grow are inside of the chamber 9 and/or culture vessel(s) 10. The monitoring system 9 may directly or indirectly view, measure, record, and transmit data. For example, the monitoring system 6 may use a pipette to obtain cells extracted from the culture vessel(s) to measure the amount of cell growth or the monitoring system 6 may use a probe inserted into each culture vessel 10 to determine the pH level (not shown). Alternatively, for example, the monitoring system 6 could use a sensor 18 positioned inside the chamber 9 or outside of the chamber 9 to measure the amount of nutrients in the chamber 9 (e.g., a gas analyzer may be used to measure and analyze the amount of carbon dioxide and oxygen in the chamber 9). As another example, the monitoring system 6 could use a sensor 18 to determine the density of the cells inside the culture vessel(s) 10 (e.g., conventional light scattering techniques could be used to measure the density inside the culture vessel(s)) (not shown). The monitoring system 6 may detect a variety of conditions, including but not limited to the pH level, oxygen level, carbon dioxide level, temperature, and density of the cells.

The channel 4 of the biolevitator 1 can be utilized to deliver nutrients that promote cell growth. Examples of required nutrients may include, but are not limited to, carbohydrates, nitrogen, vitamins, salts, and oxygen. For example, the channel 4 may deliver nutrients via a gas injected into the chamber 9, as shown in FIG. 1, and the nutrients may diffuse into the medium in the culture vessel(s) 10. Alternatively, the channel 4 may be configured to directly deliver nutrients, via gas or liquid, directly to the culture vessels 10 (not shown).

The control system 2 of the biolevitator 1 may be used, for example, to control system operation, program cell culture workflow, and/or data collection and display. For example, the control system 2 may receive information from the sensor 18 and/or the monitoring system 6 and adjust inputs to the chamber 9 to control cell growth in the culture vessels 10 or may control the direction that and the intervals in which the motion generating device 5 causes the culture vessel 10 to rotate. Also, for example, the control system 2 may determine the phase in which the cell culture workflow is by using input from the monitoring system 6 or discrete settings input into the control system 2 so that that control system 2 knows when the phases of the cell culture workflow occur. Generally, there are three phases of cell culture workflow, the stage in which cells attach to sediment within each culture vessel 10, the stage in which the cells divide and grow, and the stage in which a portion of the sediment that the cells are attached to is broken down by a solution (e.g. an enzymatic solution) so that the cells are released from the sediment. As another example, the control system 2 may receive information from the sensors 18 and/or the monitoring system 6 and display that information to the operator. The control system 2 could be used in other ways (e.g., regulating the chamber 9 environment, transmitting the conditions within the chamber 9 or culture vessel(s) 10 to alert an operator to the presence of various conditions). The control system 2 may include hardware that is operated manually or may be enhanced to include mechanical systems that operate automatically. The control system may further include software and control electronics to enable a fully automated system.

Culture Vessel(s)

Figure 4:
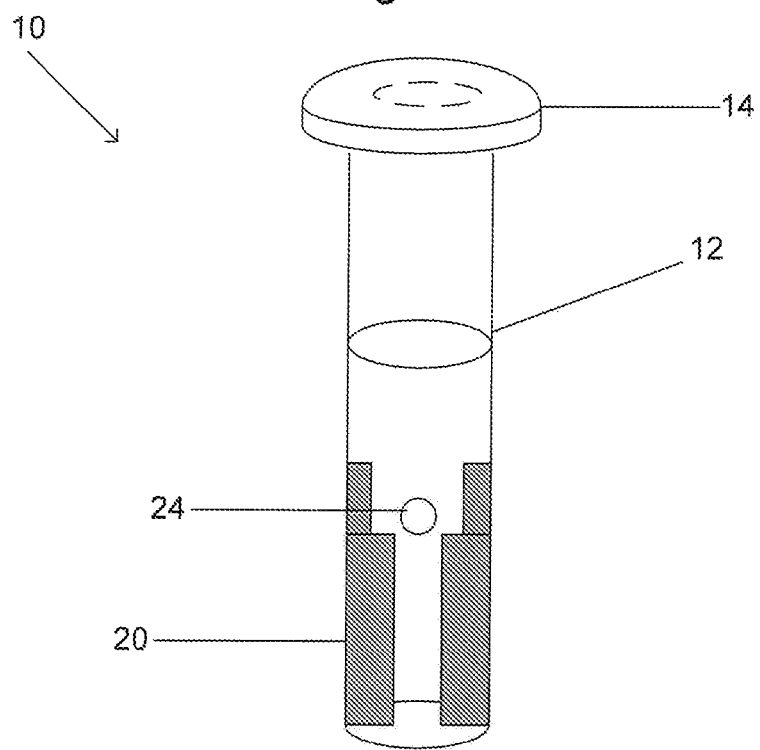
FIG. 4 is a top, side, perspective view of an embodiment of a culture vessel.
Figure 5A:
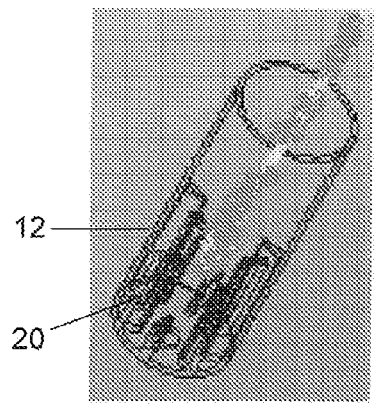
FIG. 5A is a top, side, perspective view of an embodiment of a culture vessel having a first volume.
Figure 5B:
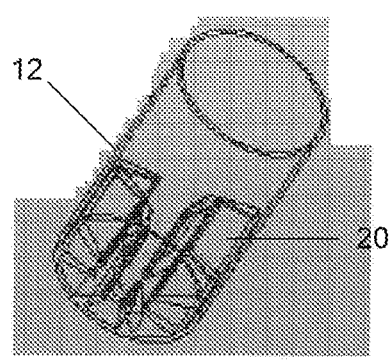
FIG. 5B is a top, side, perspective view of an embodiment of a culture vessel having a second volume.
Figure 5C:
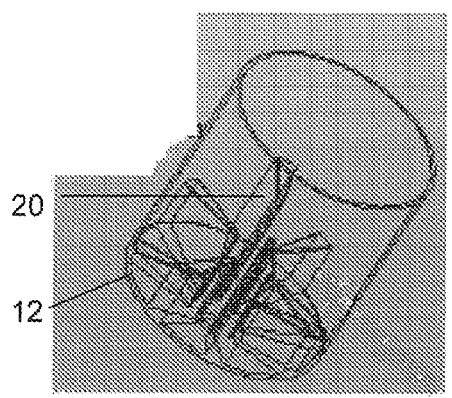
FIG. 5C is a top, side, perspective view of an embodiment of a culture vessel having a third volume.
Figure 5D:
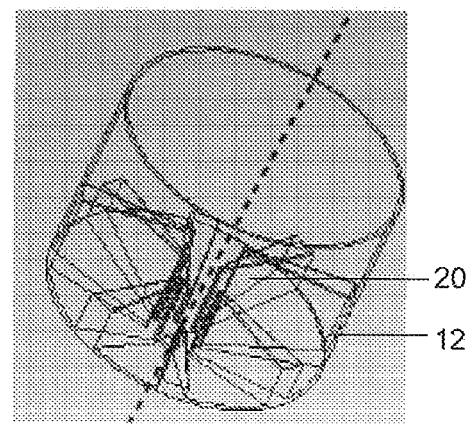
FIG. 5D is a top, side, perspective view of an embodiment of a culture vessel having a fourth volume.
Figure 5E:
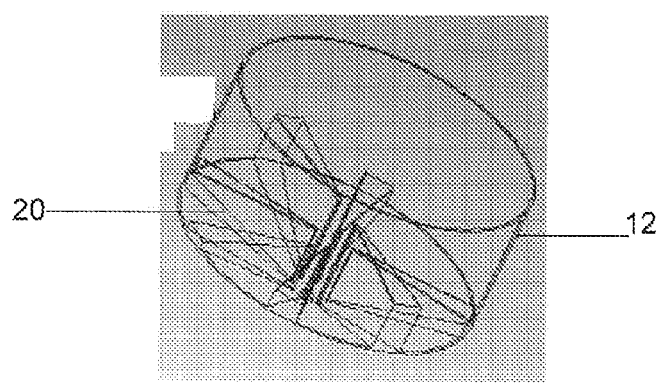
FIG. 5E is a top, side, perspective view of an embodiment of a culture vessel having a fifth volume.

According to one embodiment and as shown in FIG. 4, the culture vessel 10 may include a container 12 and a plurality of agitators 20 disposed within the container. The culture vessel 10 may also include a cap 14 configured to maintain the medium and cell within the container 12 and/or selectively isolate them from the environment.

The culture vessel 10 is a vessel for supporting cell growth that generally contains a medium, cells, and a sediment. The culture vessel 10 may also support separation of individual cells. The medium may be any medium that provides nutrients to the cells that support cell growth. The medium typically includes nutrients, salts, and other elements well known to those of skill in the art. Different cells may utilize different medium to optimize growth. The medium is provided in addition to the nutrients that are directly or indirectly provided to the culture vessel 10. The cells may be any cells suitable for being grown in a laboratory process. For example, the cells may be bacteria or human cells. The sediment may be anything capable of being lifted from the bottom of a culture vessel 10 that can also be maintained in suspension. The cells may be required to be anchored to the sediment to promote cell growth. Alternatively, the cells may be collected on the sediment or not collected on the sediment. As another option, the cells may be kept suspended so that the sediment may attract one or more of the cells. Any suitable sediment may be used. Preferably, the sediment is a microcarrier 24 when the culture vessel 10 is used to support cell growth. Preferably, the sediment is a separation bead (not shown) when the culture vessel 10 is used to support the separation of individual cells. Although FIG. 4 shows only one microcarrier 24, the culture vessel 10 may include a plurality of microcarriers 24. Details about the construction and use of microcarriers in culture vessels, including specially engineering microcarriers can be found in U.S. application Ser. No. 10/893,569, filed Jul. 19, 2004, which is herein incorporated by reference in its entirety.

The culture vessel 10, e.g., the container 12 and agitators 20, may be made of any suitable material. Preferably the culture vessel 10 is made of polystyrene. During manufacturing, the culture vessel 10 may be manufactured with non-leaching material, so that pollutants do not enter the inside of the culture vessel 10 and do not contaminate the cells. Preferably, the culture vessel 10 is manufactured from non-leaching clear polystyrene and is gamma irradiated for sterility. It is preferred that the culture vessel 10 is formed as a single unitary device. However, the culture vessel could be formed in portions that are connected together. For example, the container 12 and agitators 20 could be formed separately and connected together (e.g., by any suitable glue or adhesive). Furthermore, it is preferred that the culture vessel 10 is formed of a single material. However, it could be formed of multiple materials. For example, the container 12 could be formed of one material and the agitators 20 could be formed of another material.

The container 12 may be formed in a variety of sizes and shapes. Exemplary configurations of a container 12 are shown in FIGS. 5A-5E. According to a first embodiment shown in FIG. 5A, a container 12 may have a volume of about 50 mL, with an inner diameter of about 2.85 cm, and an inner height of about 7.8 cm. According to a second embodiment shown in FIG. 5B, a container 12 may have a volume of about 100 mL, with an inner diameter of about 4.03 cm, and an inner height of about 7.8 cm. According to a third embodiment shown in FIG. 5C, a container 12 may have a volume of about 250 mL, with an inner diameter of about 6.37 cm, and an inner height of about 7.8 cm. According to a fourth embodiment shown in FIG. 5D, a container 12 may have a volume of about 500 mL, with an inner diameter of about 9.01 cm, and an inner height of about 7.8 cm. According to a fifth embodiment shown in FIG. 5E, a container 12 may have a volume of about 1,000 mL, with an inner diameter of about 12.75 cm, and an inner height of about 7.8 cm. The height of the aforementioned examples is the same so that the containers 12 may fit in conventional handling robotic devices (e.g., a Hamilton MICROLAB STAR liquid handling workstation), while simultaneously having the inside of the containers 12 accessible. Although, all of the aforementioned exemplary containers 12 have the same height, other heights for the containers 12 are possible. Additionally, although a variety of volumes of the container 12 are provided, other volumes of the container 12 are possible. For example, the container 12 may be larger than 1,000 mL. Additionally, the volume of the container 12 may be several hundreds of milliliters. One of skill in the art could also construct a container 12 with at least 10, 100, or 1000 liters, as needed for the growth of a culture. The aforementioned examples of the height and volume of the container 12 should not be considered limiting.

Figure 6A:
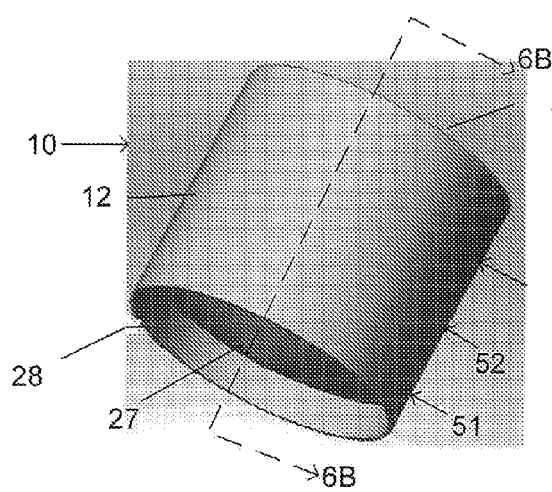
FIG. 6A is a bottom, side, perspective view of an embodiment of a container included in a culture vessel.

FIG. 6A provides a bottom, perspective view of an embodiment of container 12, which serves to illustrate an exemplary shape of the container 12 is shown in FIG. 6 and helps to aid in identifying its features. As shown in FIG. 6, the container 12 may be cylindrically shaped. However, other shapes of the container 12 are also possible. As shown in FIG. 6A, the container 12 may include a bottom 27, a bottom portion 51, an intermediate portion 52, a top portion 53, and an opening 40.

Figure 6B:
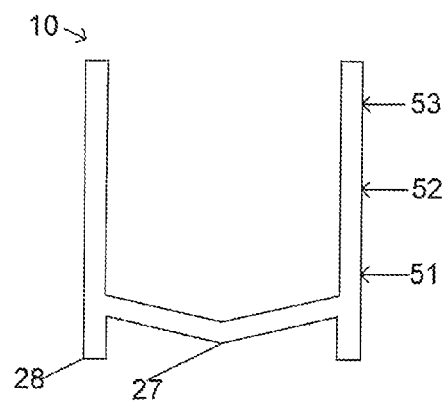
FIG. 6B is a side cross sectional view of the container of FIG. 6A taken along 6B-6B.

The bottom 27 of the container 12 can be shaped such that the cells collect at the bottom of the container 12 and the cells remain accessible to tools, even though a plurality of agitators are included in the culture vessel. Any suitable shape for the bottom 27 of the container 12 that allows the cells to remain accessible to tools may be used. Preferably, the bottom 27 of the container 12 is sloped. If the bottom 27 of the container 12 is sloped, the bottom 27 may include a skirted exterior edge 28. As shown in FIG. 6B, the skirted exterior edge 28 can provide clearance that allows the bottom 27 to be sloped while at the same time maintaining the stability of the container 12. Any suitable tool, such as a pipette or a robotic arm, may be used to access the bottom 27 of the container 12. In general, the tool enters the container 12 through the opening 40 of the container 12.

The plurality of agitators 20 of the culture vessel 10 are positioned to contact the medium received in the container 12 and are configured to promote suspension of the cells in the medium when the agitators 20 oscillate. Specifically, when the agitators 20 oscillate, the agitators 20 generate enough force per unit area to lift the cells anchored on the sediment from the bottom portion 51 of the container 12. When the cells anchored on the sediment are lifted, the fluid flow created by the oscillation of the agitators 20 moves the cells anchored on the sediment such that the cells anchored on the sediment repeatedly travel from the bottom portion 51 of the container 12 to the intermediate or top portions 52, 53 of the container and then back down to the bottom portion 51 of the container 12. The constant traversal of the cells along the length of the container 12 allows all of the cells in the container 12 to receive enough oxygen and ensures that the cells have access to the nutrients and medium, such that all of the cells are given the opportunity to adequately grow.

The plurality of agitators 20 of the culture vessel are also configured to promote suspension of the separation beads in the medium when the agitators 20 oscillate. Specifically, when the agitators 20 oscillate, the agitators 20 generate enough force per unit area to lift the separation beads from the bottom portion 51 of the container 12. When the separation beads are lifted, the fluid flow created by the oscillation of the agitators 20 moves the separation beads such that the separation beads are able to separate the cells. When moving, the separation beads repeatedly travel from the bottom portion 51 of the container 12 to the intermediate or top portions 52, 53 of the container 12 and then back down to the bottom portion 51 of the container 12. The constant traversal of the separation beads along the length of the container 12 allows the separation beads to separate all of the cells in the container 12.

The agitators 20 oscillate because the agitators 20 are at least one of coupled to and formed integrally with the container 12 such that there is no relative movement between the agitators 20 and the container 12. Due to this absence of relative movement, when the motion generating device 5 causes the container 12 to oscillate, the agitators 20 will likewise oscillate.

The motion generating device 5 can be controlled to oscillate the agitators 20 at any desired rate and through any desired range of motion. Preferably, the agitators oscillate by reversing their rotation every half-revolution. Other intervals or patterns of oscillation of the agitators 20 may be used depending on, for example, the type of cells being grown in the container 12.

The oscillation of the agitators 20 allows the cells to experience minimal shear and acceleration forces. Conventional mechanisms exert excessive shear and acceleration forces because, for example, the mechanisms only allow rotation of the spinner flask or the tissue culture container in one direction or have limited surface area resulting in the need for the introduction of more kinetic energy per available surface area for particle dispersing. Excessive shear forces lead to cell loss and cell death. The agitators 20, however, oscillate, thus allowing for a continuous back-and-forth rotation of the container 12.

Figure 7:
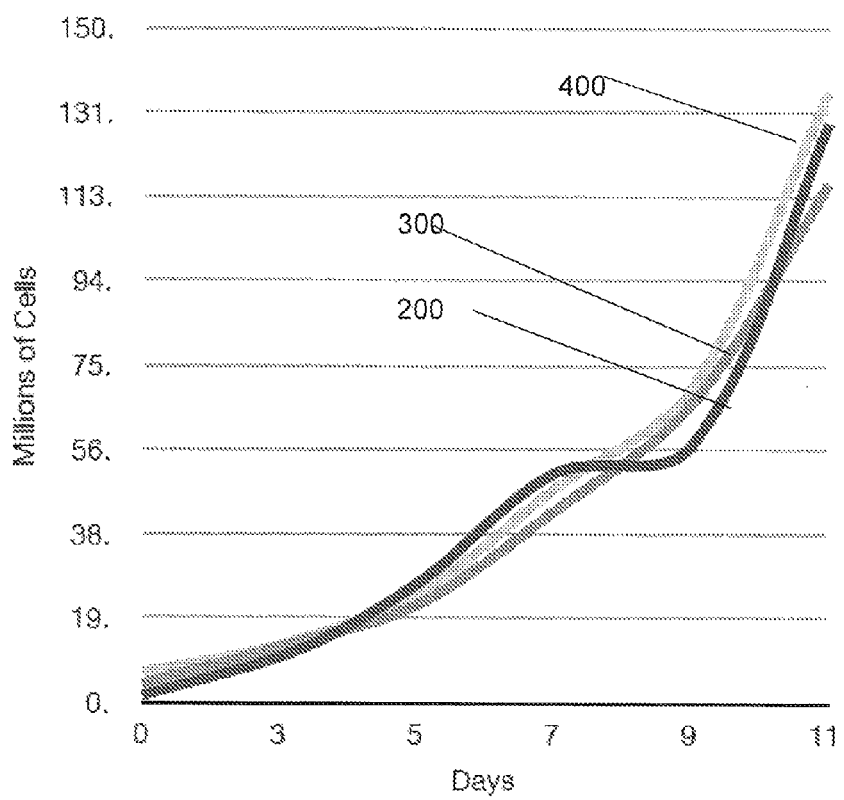
FIG. 7 is a graph showing millions of cells grown per days for three exemplary culture vessels.
Figure 8:
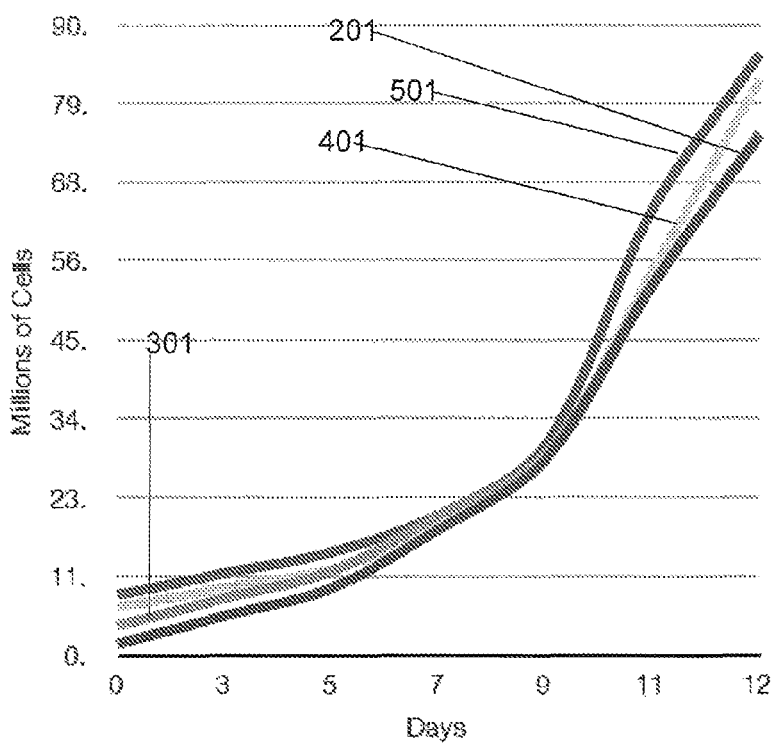
FIG. 8 is a graph showing millions of cells grown per days for four of TPP's tissue cultures and centrifuge tubes.
Figure 9:
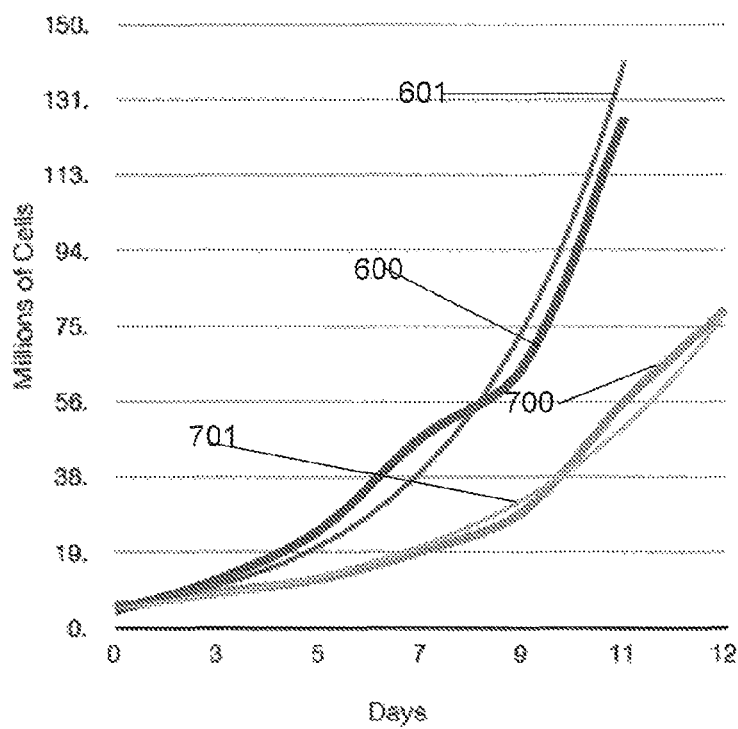
FIG. 9 is a graph comparing the millions of cells grown per days for the average of the three different exemplary culture vessels (graphed in FIG. 7) as compared to the average of the four different TPP tissue cultures and centrifuge tubes (graphed in FIG. 8) as well as a best fit curve for the average of the three different exemplary culture vessels and a best fit curve for the four different TPP tissue cultures and centrifuge tubes.

FIGS. 7-9 illustrate an example of the increase in cell yield that can be realized through the use of agitators 20 as compared to a conventional mechanism, such as TPP's tissue culture and centrifuge tube. In this example the difference in yield is significant (p=0.0005).

FIG. 7 shows the growth of the cells per the number of days that the cells will grow before cell death occurs, when agitators are used to promote cell growth in three different culture vessels. The only difference between the culture vessels is that a different amount of cells are initially placed in each culture vessel. The culture vessels are subject to the same environmental conditions. For example, line 200 shows the cell growth in a first culture vessel over a period of time where a first amount of cells are initially placed in the first culture vessel, line 300 shows the cell growth in a second culture vessel over a period of time where a second amount of cells are initially placed in the second culture vessel, and line 400 shows the cell growth in a third culture vessel over a period of time where a third amount of cells are initially placed in the third culture vessel. As shown in FIG. 7, there is not that much variation between lines 200, 300, and 400, thereby showing that initially placing different amounts of cells in different culture vessels does not generally affect the overall amount of cells that grow.

FIG. 8 shows the growth of the cells per the number of days that the cells will grow before cell death occurs for four different TPP tissue cultures and centrifuge tubes. The only difference between the TPP tissue cultures and centrifuge tubes is that a different amount of cells are initially placed in each TPP tissue cultures and centrifuge tubes. The TPP tissue cultures and centrifuge tubes are subject to the same environmental conditions. For example, line 201 shows the cell growth in a first TPP tissue culture and centrifuge tube over a period of time where a first amount of cells are initially placed in the first TPP tissue culture and centrifuge tube, line 301 shows the cell growth in a second TPP tissue culture and centrifuge tube over a period of time where a second amount of cells are initially placed in the second centrifuge tube, line 401 shows the cell growth in a third TPP tissue culture and centrifuge tube over a period of time where a third amount of cells are initially placed in the third centrifuge tube, and line 501 shows the cell growth in a fourth TPP tissue culture and centrifuge tube over a period of time where a fourth amount of cells are initially placed in the fourth TPP tissue culture and centrifuge tube. As shown in FIG. 8, there is not that much variation between lines 201, 301, 401, and 501, thereby showing that initially placing different amounts of cells in different TPP tissue cultures and centrifuge tubes does not generally affect the overall amount of cells that grow.

FIG. 9 shows the average of the individual cultures plotted for the growth of cells per the amount of days, when the agitators in the culture vessels were used to help promote cell growth as opposed to when TPP's tissue cultures and centrifuge tubes were used to grow cells, and an exponential curve fit to the average individual cultures plotted. Specifically, line 600 shows the average of the three culture vessel lines shown in FIG. 7 and line 700 shows the average of the four TPP tissue cultures and centrifuge tubes lines shown in FIG. 8. Lines 601 and 701 show the exponential curves fit to the average line for the culture vessels and the average line for the TPP tissue cultures and centrifuge tubes respectively. The exponential curve shown in line 601 is $y=2.94e+6e0.645x$ and the exponential curve shown in line 701 is $y=3.365e+6e0.4495x$. As seen in the comparison graph, FIG. 9, the average doubling time for the case where the agitators in the culture vessels were used to help promote cell growth was 2.3 days as opposed to 3.1 days for TPP's tissue cultures and centrifuge tubes leading to a significance difference in yield of (p=0.0005).

The size, shape, and position of the agitators 20 within the container 12 also allows the cells to experience minimal shear and acceleration forces. The shear force is related to the power applied to a container 12 by an external mixing force per unit of volume of the container 12 and the surface area of the mixing elements. The larger the surface area on the agitators 20, the more stirring one obtains for each rotational motion. The larger surface area enables the agitators 20 to affect more cells than the smaller surface area. Similarly, the shape/orientation of the agitators 20 may also impact the power needed to agitate the medium in the container 12.

FIGS. 10A to 21C show some of the shapes and positions of the agitators 20 within a container 12 where all of the containers 12 shown in FIGS. 10A to 21C are the same height, so that the containers 12 may fit in a conventional handling robotic device. FIGS. 10A and 10B, for example, show an exemplary container 12 including agitators 20 that extend from the bottom portion 51 of the container 12 to the intermediate portion 52 of the container 12. The lateral cross section of each of the plurality of agitators 20 shown in FIGS. 10A and 10B, as shown in FIG. 10C, is triangularly shaped.

Figure 11C:
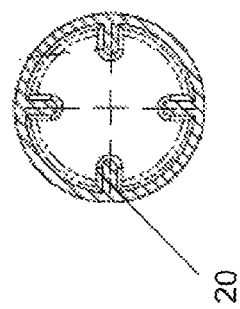
FIG. 11C is a top, cross-sectional view of the culture vessel of FIG. 11B taken along line 11C-11C.
Figure 11B:
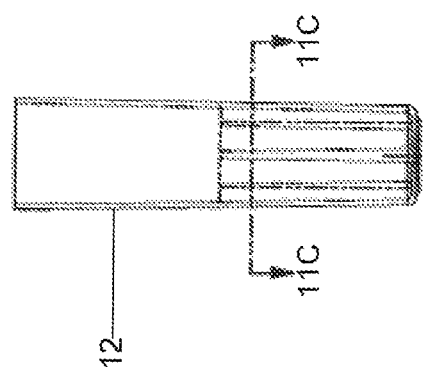
FIG. 11B is a side, cross sectional view of the culture vessel of FIG. 11A taken along line 11B-11B.
Figure 11A:
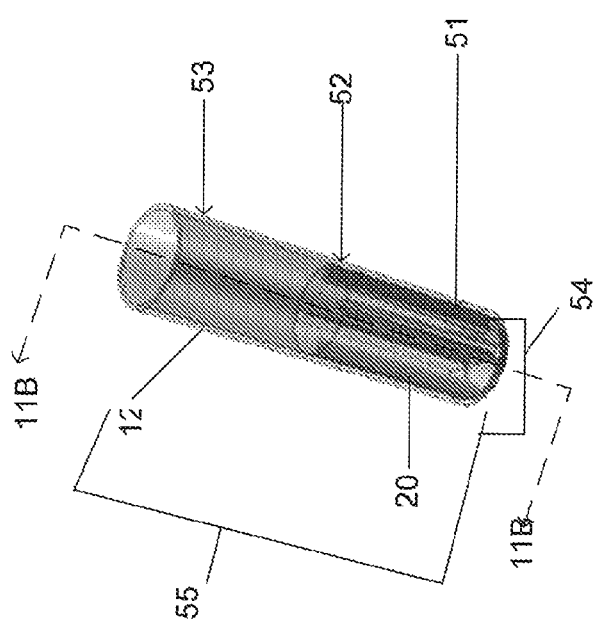
FIG. 11A is a top, side, perspective view of an embodiment of a culture vessel including a plurality of agitators.
Figure 15C:
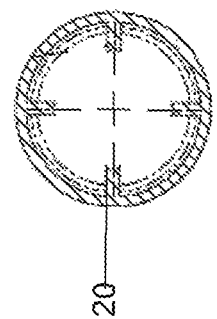
FIG. 15C is a top, cross sectional view of the culture vessel of FIG. 15B taken along line 15C-15C.
Figure 15B:
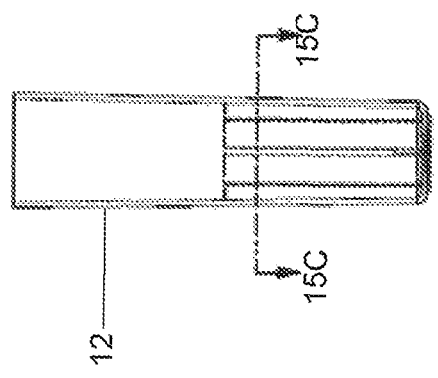
FIG. 15B is a side, cross sectional view of the culture vessel of FIG. 15A taken along line 15B-15B.
Figure 15A:
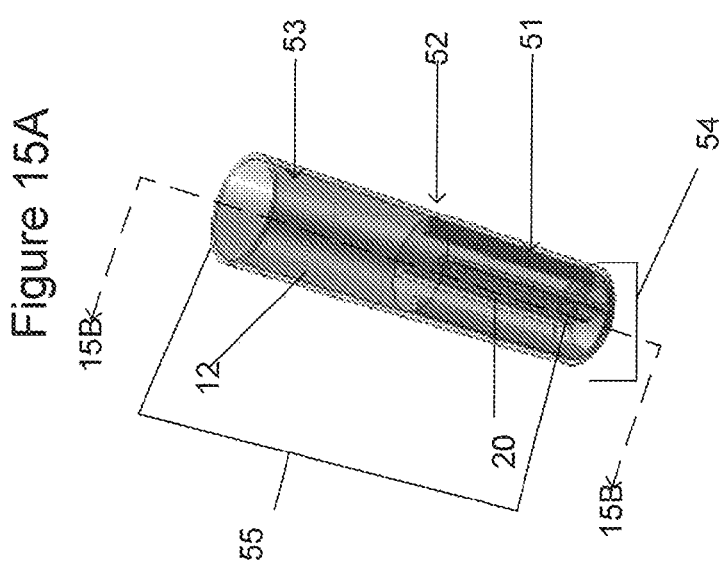
FIG. 15A is a top, side perspective view of an embodiment of a culture vessel including a plurality of agitators.

FIGS. 11A, 11B, 12A, 12B, 13A, 13B, 14A, 14B, 15A, 15B, 21A, and 21B also include agitators 20 that extend from the bottom portion 51 of the container 12 to the intermediate portion 52 of the container 12. The lateral cross section of each of the plurality of agitators 20 of FIGS. 11A, 11B, 12A, 12B, 13A, 13B, 14A, 14B, 15A, 15B, 21A, and 21B however, is different from the lateral cross section of each of the plurality of agitators 20 of FIGS. 10A and 10B. The lateral cross section of each of the plurality of agitators 20 of FIGS. 11A and 11B, as shown in FIG. 11C, is U-shaped. The lateral cross section of each of the plurality of agitators 20 of FIGS. 12A and 12B, as shown in FIG. 12C, is substantially U-shaped. The lateral cross section of each of the plurality of agitators 20 of FIGS. 13A and 13B, as shown in FIG. 13C, is cone shaped. The lateral cross section of each of the plurality of agitators 20 shown in FIGS. 14A and 14B, as shown in FIG. 14C, is triangularly shaped. The lateral cross section of each of the plurality of agitators 20 of FIGS. 15A and 15B, as shown in FIG. 15C, is substantially U-shaped. The lateral cross section of each of the plurality of agitators 20 of FIGS. 21A and 21B, as shown in FIG. 21C, is rectangular shaped.

Figure 17C:
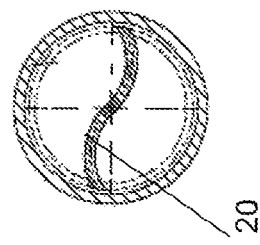
FIG. 17C is a top, cross sectional view of the culture vessel of FIG. 17B taken along line 17C-17C.
Figure 17B:
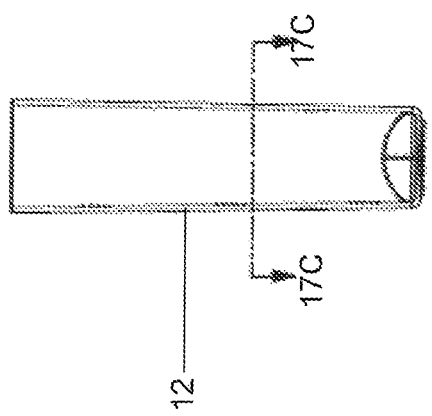
FIG. 17B is a side, cross sectional view of the culture vessel of FIG. 17A taken along line 17B-17B.
Figure 17A:
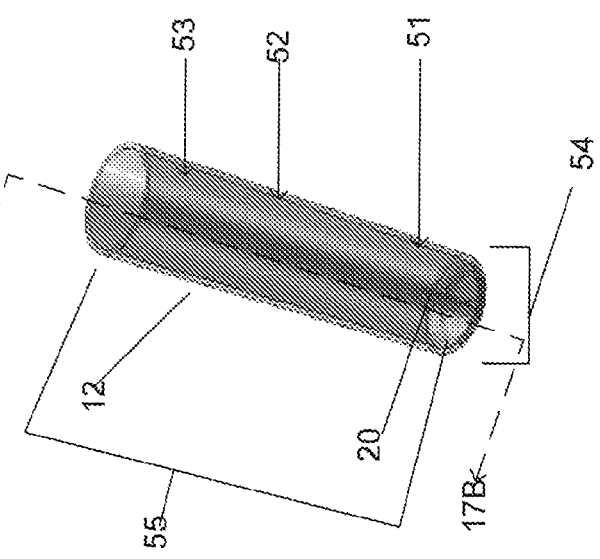
FIG. 17A is a top, side perspective view of an embodiment of a culture vessel including a plurality of agitators.
Figure 19C:
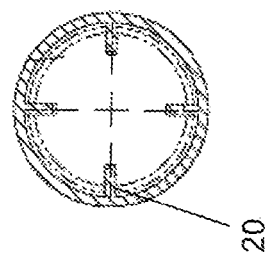
FIG. 19C is a top, cross sectional view of the culture vessel of FIG. 19B taken along line 19C-19C.
Figure 19B:
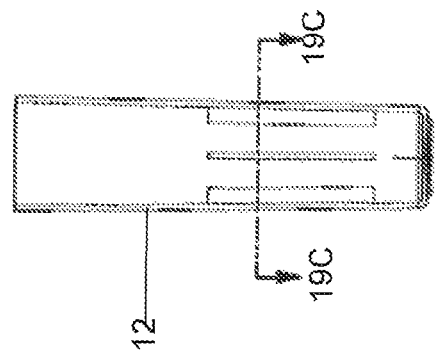
FIG. 19B is a side, cross sectional view of the culture vessel of FIG. 19A taken along line 19B-19B.
Figure 19A:
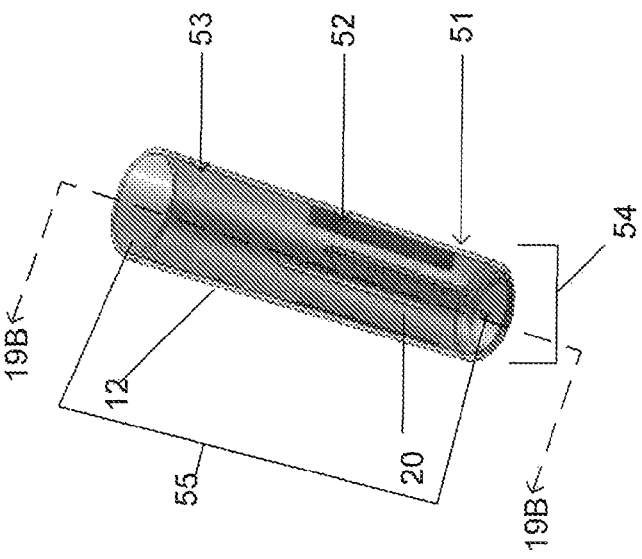
FIG. 19A is a top, side perspective view of an embodiment of a culture vessel including a plurality of agitators.

FIGS. 16A and 16B, for example, show an exemplary container 12 including agitators 20 that only extend along the bottom portion 51 of the container 12. FIGS. 17A, 17B, 18A, and 18C also include agitators 20 that only extend along the bottom portion of the container 12. The lateral cross section of each of the plurality of agitators 20 shown in FIGS. 16A and 16B, as shown in FIG. 16C, is rectangularly shaped. The lateral cross section of each of the plurality of agitators 20 of FIGS. 17A, 17B, 18A, and 18B, however, is different from the lateral cross section of each of the plurality of agitators of FIGS. 16A and 16B. The lateral cross section of each of the plurality of agitators of FIGS. 17A and 17B, as shown in FIG. 17C, is sinusoidally shaped. The lateral cross section of each of the plurality of agitators 20 of FIGS. 18A and 18B, as shown in FIG. 18C, is oval shaped. FIGS. 19A, 19B, 20A, and 20B include agitators that extend from the bottom portion 51 of the container 52 to the intermediate portion 53 of the container 12. Unlike for example FIGS. 16 and 16B, however, the agitators 20 of FIGS. 19A, 19B, 20A, and 20B do not extend from the bottom wall portion 54 of the container 12. The lateral cross section of each of the plurality of agitators 20 of FIGS. 19A, 19B, 20A, and 20B, as shown in FIGS. 19C and 20C, is rectangularly shaped. While most of the agitators 20 shown in FIGS. 10A to 21C shown agitators 20 that extend from the bottom wall portion 54 and the side wall portion 55 of the container 12, FIGS. 19A, 19B, 20A, and 20B show agitators 20 that only extend from the side wall portion 55 of the container 12. FIGS. 18A and 18B show agitators 20 that only extend from the bottom wall portion 54 of the container 12.

The agitators 20 make it easier to dispose of the culture vessel 10 after use of the culture vessel 10 is completed and its contents are discarded as opposed to conventional mechanisms. Conventional mechanisms consisted of numerous parts. For example, a conventional mechanism like the spinner flask included the flask and a suspended impeller not coupled to or formed integrally with the flask. Conventional mechanisms were generally either reused or disposed. Reusing the conventional mechanisms required separating the flask from the suspended impeller and cleaning the flask and the suspended impeller. Often it takes significant effort to clean the conventional mechanisms and thus is less efficient than integrated disposable devices, such as the culture vessel 10. When disposing of the conventional mechanism, operators also had to undergo the time consuming task of separating the flask from the suspended impeller. The agitators 20, however, are at least one of coupled to and integrally formed with the container 10 such that an operator desiring to dispose of the agitators 20 and the container 10 does not have to spend time separating the two from one another.

Figure 22:
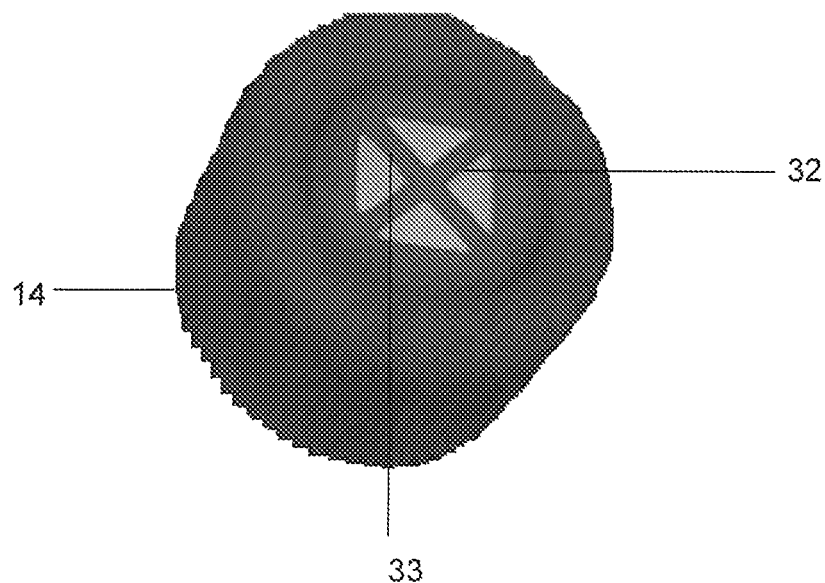
FIG. 22 is a top view of an embodiment of a cap.

The cap 14 of the culture vessel 10 may be coupled to the container 12 to prevent contaminants from entering the container 12, while simultaneously allowing sufficient aeration to the inside of the container 12 so that the cells may grow. As shown in FIG. 22, the cap 14 may include a plurality of openings 33. A vent 32 may be placed inside of the cap 14 to cover the openings 33. Any suitable vent, for example a filter, may be used. The vent 32 may be attached to the inside of the cap 14. For example, the vent 32 may be glued to the cap 14. The vent 32 protects contaminants from entering the inside of the container 10, while simultaneously allowing oxygen to enter the inside of the container 10 so that the cells inside the container 10 may grow.

Figure 23:
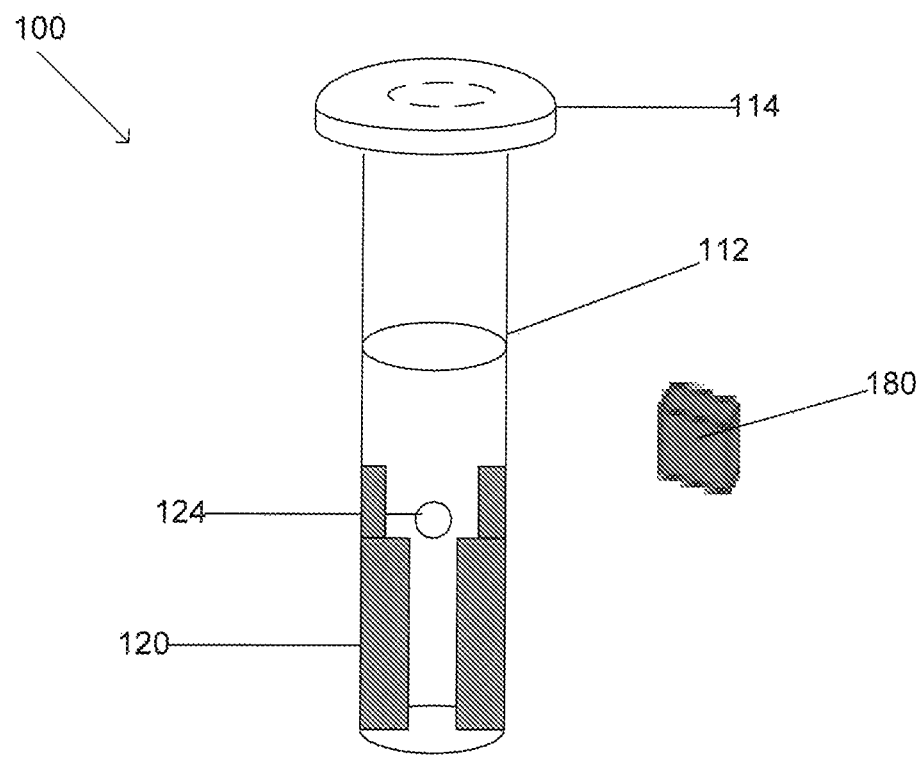
FIG. 23 a top, side, perspective view of an embodiment of a culture vessel and a magnet.

According to a another embodiment, as shown in FIG. 23, the culture vessel 100 may include a container 112, a plurality of agitators 120, a magnet 180, and a cap 114 (not shown). The agitators 120 and the cap 114 operate and are structured the same way as the agitators described in the prior embodiments.

The magnet 180 may be used to attract a sediment 124 located in the container 112 of the culture vessel 100. The magnet 180 may be a permanent magnet or an electromagnet. The magnet 180 creates a varying magnetic field. The sediment 124 may be any suitable device capable of supporting the growth of cells that reacts to a magnetic field. Preferably, the sediment 124 is a microcarrier made of a hydrogel composition that includes a ferromagnetic or paramagnetic material. Further details about the use of magnets, ferromagnetic particles, and paramagnetic particles to help grow cells in a culture vessel can be found in U.S. application Ser. No. 10/893,569, filed Jul. 19, 2004. The magnetic field created by the magnet 180 attracts the ferromagnetic or paramagnetic material of the microcarrier 124.

The attraction of the microcarrier 124 to the magnet 180 enhances the suspension of the cells in the container 112. The magnet 180 is continuously moved relative to the container 112 to vary the magnetic field that attracts the microcarrier 124. Because the magnetic field is varied, the suspension of the cells as caused by the agitators 120, is enhanced. The magnet 180 may be continuously moved in any direction. For example, the magnet may be moved vertically to control the positions of the cell in the vertical direction. As another example, the magnet can be moved horizontally and/or rotationally to control the concentration of cells in a given location. Combinations of the above movements can also be utilized. The amount and/or type of movement can also be adjusted. For example, the magnet 180 may be continuously moved in the same direction or the magnet 180 may be oscillated. Preferably, the magnet 180 is oscillated. The magnet 180 may be moved by an operator or by any suitable device. In order to more uniformly affect the microcarrier 124, the magnet 180 is preferably moved by a device.

The magnet 180 may be placed at any desired location in relation to the container 112 that will create the desired movement of the microcarrier 124. When a container 112 is relatively small, for example, a magnet may be placed above, below, or on the side of the container 112. FIG. 23, for example, shows a magnet 180 placed on the side of the container 112. Although FIG. 23 shows one magnet 180, it should be understood that there may be more magnets.

When a container 112 is relatively large, a magnet 180 placed above, below, or on the side of the container 112 may not produce enough of a magnetic force to attract the microcarriers. In such situations, the magnet 180 may be inserted at or near the center of the container 112. Preferably, as shown in FIGS. 24A-25B, the container 112 will include a magnetic insert 190 that is capable of receiving a magnet 180. Preferably, the magnetic insert 190 is located, as shown in FIGS. 24A-25B, along a center longitudinal axis of the container 112 and extends along at least a portion of the container's 112 length. Such configurations could use or not use an exterior magnet 180, such as shown in FIG. 23.

Although, the specification generally refers to the culture vessel 10 being formed as a single unitary device where the container 12 and the agitators 20 are formed together, the container 12 and the agitators 20 could be formed separately. For example, the container could be any suitable container, such as a falcon tube, and the agitators could be included on a sheet. The agitators may be included on the sheet by being integrally formed with the sheet or attached to the sheet after the sheet is formed.

The sheet and the agitators may be made of the same or different material. Preferably, the sheet is made of a material that creates enough tension between the inner surface of the container and the outer surface of the sheet, when the sheet is within the container, that the sheet adheres to the inner surface of the container. The outer surface of the sheet is the side of the sheet that does not include the agitators. In addition to including the agitators, the sheet may include perforations.

Initially, the sheet that includes the agitators could be stored in a sterilized and prepackaged container. When a user wishes to place the sheet inside of the container, a user could open the prepackaged container, manipulate the sheet to fit within the container and place the sheet within the container. The sheet can be manipulated in any suitable way. For example, the sheet can be rolled up to fit within the container. When the sheet is placed within the container, ends of the sheet may or may not overlap.

One versed in the art would appreciate that there may be other embodiments and modifications within the scope and spirit of the disclosure. Accordingly, all modifications attainable by one versed in the art from the present disclosure, within its scope and spirit, are to be included as further embodiments of the present disclosure. The scope of the following claims and their equivalents is intended to cover such embodiments, modifications, and alternative designs.

What is claimed is:

1. A culture vessel, comprising:
    a container having an open top and closed bottom for receiving a medium and cells; and
    a plurality of agitators sinusoidally configured, with respect to one another, along the inside of the container, wherein the sinusoidally configured agitators are positioned to contact the medium when received in the container,
    wherein sinusoidally configured agitators refers the distance between the top of each agitator and the top of the container varying such that a line connecting the tops of the agitators forms a sine wave;
    wherein a lateral cross section of each agitator is substantially rectangularly shaped;
    wherein the agitators are coupled to and formed integrally with the container such that there is no movement therebetween.

2. The culture vessel of claim 1, wherein the bottom of the container is shaped such that the cells collect at the bottom of the container and the cells remain accessible for recovery from the bottom of the container.

3. The culture vessel of claim 1, wherein a magnet positioned external to the container is configured to attract an engineered microcarrier suitable for growing the cells comprising a hydrogel composition capable of providing a substrate that will support the growth of cells, wherein said hydrogel composition further comprises at least one material which renders the microcarrier responsive to a magnetic force.

4. The culture vessel of claim 3, wherein the magnet is further moved so as to enhance either a suspension or concentration of the cells in the container.

5. The culture vessel of claim 1, wherein the container includes a bottom portion, an intermediate portion, and a top portion, and the agitators extend from the bottom portion to at least the intermediate portion.

6. The culture vessel of claim 1, wherein the container includes a bottom wall portion and a side wall portion, and the agitators project from the side wall portion.

7. The culture vessel of claim 1, wherein the container includes a bottom wall portion and a side wall portion, and the agitators project from the bottom wall portion.

8. The culture vessel of claim 1, wherein the agitators are configured such that oscillation of the agitators causes the medium to oscillate and wherein the oscillation of the medium promotes movement of the cells along a longitudinal direction of the container and reduces shear forces acting on the cells.

9. The culture vessel of claim 1, wherein more agitators are positioned at a bottom portion of the container than at a top portion of the container so as to enable an upward force vector to encourage suspension of the cells in the medium.

10. The culture vessel of claim 1, further comprising a cap coupled to the container and configured to at least one of prevent contaminants from entering the container and allow the medium to enter the container.

11. The culture vessel of claim 1, further comprising a sensor configured to sense a condition inside the culture vessel.

\* \* \* \* \*